United States Patent [19]

Angerer

[11] Patent Number: 4,736,192
[45] Date of Patent: Apr. 5, 1988

[54] EXCITATION CIRCUIT FOR PIEZO-ELECTRIC SOUND GENERATORS

[75] Inventor: Richard Angerer, Oberhaching, Fed. Rep. of Germany

[73] Assignee: Siemens Aktiengesellschaft, Berlin and Munich, Fed. Rep. of Germany

[21] Appl. No.: 622,127

[22] Filed: Jun. 19, 1984

[30] Foreign Application Priority Data

Aug. 10, 1983 [DE] Fed. Rep. of Germany ....... 3328907

[51] Int. Cl.⁴ ................................................ G08B 3/00
[52] U.S. Cl. .................................. 340/384 E; 331/158
[58] Field of Search ...................... 340/384 E, 384 R; 331/158, 116 R

[56] References Cited

U.S. PATENT DOCUMENTS 3,989,963  5/1975  Giaccardi .
4,010,447  3/1977  Podowski ........................ 340/384 E
4,164,735  8/1979  Salem ............................. 340/384 E

FOREIGN PATENT DOCUMENTS 2823155  12/1978  Fed. Rep. of Germany .
2104257  3/1983  United Kingdom .
2104273  3/1983  United Kingdom .

OTHER PUBLICATIONS

"Radio Engineers Handbook" by Terman, pp. 494-497, McGraw-Hill, copyright 1943.

Primary Examiner—John W. Caldwell, Sr.
Assistant Examiner—Tyrone Queen

[57] ABSTRACT

An excitation circuit wherein the energy of a charged coil is discharged via a sound generator. A coil and a capacitance of the sound generator are tuned to one another such that a corresponding oscillatory frequency is identical to a predetermined resonant frequency of the sound generator.

6 Claims, 2 Drawing Sheets

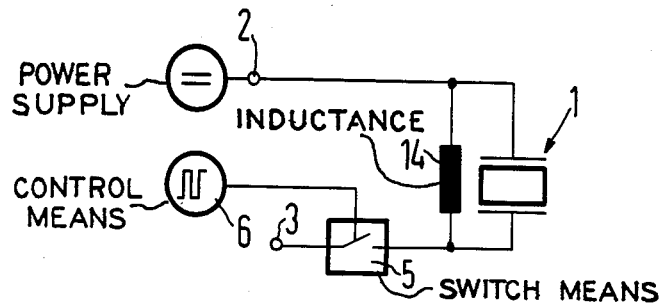
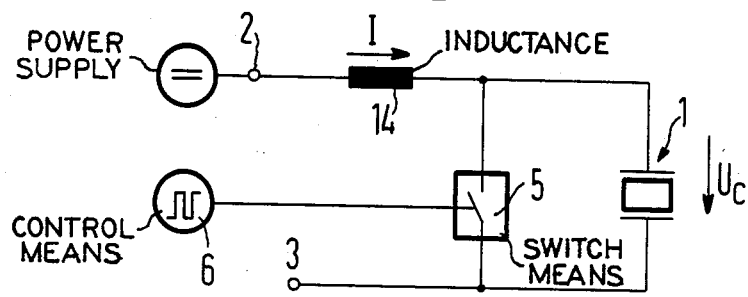
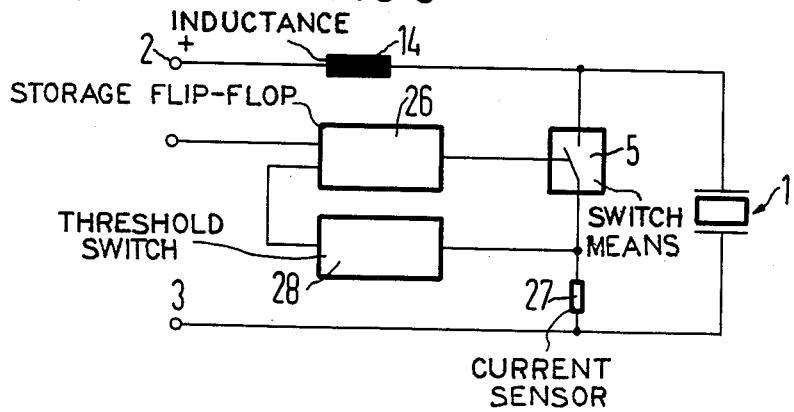

EXCITATION CIRCUIT FOR PIEZO-ELECTRIC SOUND GENERATORS

BACKGROUND OF THE INVENTION

The present invention relates to an excitation circuit having a piezo-electric sound generator, power supply terminals therefor, an inductance associated with the piezo-electric sound generator, and a switching unit for interrupting power feed to the piezo-electric generator.

It is known from FIG. 5 of German Pat. No. 28 23 155, FIG. 1 of British Pat. No. 2,104,257A, and FIG. 1 of British Pat. 2,104,273, all incorporated herein by reference, to employ an excitation circuit as shown in FIG. 1 herein for exciting oscillations of a piezo-electric sound generator. The piezo-electric sound generator 1 and a switch 5 lie in series with the terminals 2 and 3 for the power supply. The inductance 14 is charged with electrical energy as soon as an electrical voltage is present between the terminals 2 and 3 and the switch is closed. When switch 5 is opened, through actuation by a control means 6, the electric current flowing through the inductance 14 suddenly collapses. This produces an electrical impulse collision excitation for the sound generator 1 which is thereby induced to oscillate. It is not only the oscillation having the fundamental wave resonance of the sound generator 1 which is excited. Also other oscillation modes are excited. This is a disadvantage of this known circuit. A further disadvantage is that relatively high electrical voltage must be applied between the terminals 2 and 3 in order to generate significant acoustic power.

The prior art discussed above with reference to the publications and also from German Pat. No. 27 07 524, incorporated herein by reference, has been improved by providing a rectification of the voltage generated with the assistance of the inductance and to feed the transducer with this d.c. voltage. In order to achieve electroacoustical oscillations of the dc-fed transducer, however, the known switch is driven with the prescribed oscillation frequency of the transducer, i.e. induced oscillations of the transducer are generated. But the problem thus arises of being able to govern the mutual tuning of this control frequency and the natural frequency of such a transducer, the latter varying as a function of the respective operating conditions. In order to resolve this problem, German Pat. No. 2,219,761, incorporated herein by reference, provides for the additional employment of a feedback, this involving considerable added expense.

SUMMARY OF THE INVENTION

An object of the present invention is to specify as simple as possible an excitation circuit with which a piezo-electric sound generator can be excited or operated in only one oscillation mode insofar as possible.

Given an excitation circuit according to the invention, an inductance is provided in series with the sound generator between the power supply terminals. Switch means are provided in parallel with the sound generator and in series with the inductance across the power supply terminals. A value of the inductance and a capacitance of the sound generator are tuned with respect to one another such that a frequency of a resulting oscillation circuit is identical to a predetermined resonant frequency of the sound generator.

The invention is based on the idea of shifting the tuned frequency actual voltage supply source to correspond with the excitation circuit according to the invention. The only thing required for this purpose is an inductance that lies between the terminals 2 and 3 in series with the parallel circuit which is comprised of the acoustic transducer and an element with a switch function.

BRIEF DESCRIPTION OF THE DRAWINGS

FIG. 1 is a schematic diagram of a prior art circuit;
FIG. 2 is a diagram of a circuit according to the invention;
FIGS. 3 to 5 are further developments of a circuit according to the invention.

DESCRIPTION OF THE PREFERRED EMBODIMENTS

Figure 4:
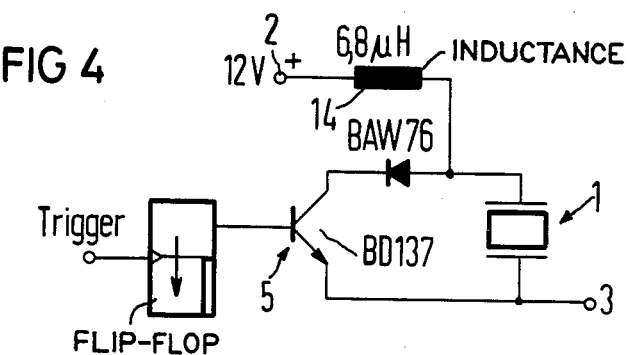

FIG. 2 shows the inductance 14 together with the elements already described in FIG. 1.

In order to explain the operating mode and function of the excitation circuit of FIG. 2, let it be assumed that the supply voltage is already present at the terminals 2 and 3. The switch 5 is closed. An electric current I flows through the inductance 14 and across the closed switch 5. As controlled by the function of control means or element 6, when the switch 5 is now opened, an extremely high current change occurs in the inductance 14. This leads to the occurrence of a high electrical voltage at the switch 5 and thus at the sound generator 1.

Since the resonant frequency of the series oscillating circuit comprised of sound generator 1 and inductance 14 is selected such that it coincides with the selected, mechanical resonant frequency of the sound generator 1, particularly by means of a corresponding dimensioning of this inductance 14, a resonant frequency excitation of the sound generator 1 follows. The sound generator receives its electrical excitation practically only at this selected resonant frequency. This leads to the fact that undesired incidental oscillation modes are avoided.

The maximum electrical voltage appearing at the terminals of the sound generator 1 when the switch 5 is opened has a considerable voltage rise in comparison to the supply voltage that is present at the terminals 2 and 3.

Fundamentally, the following physical relationships apply to the invention:

$$I(t) = 1/L \int_0^T U_L(t)\, dt \approx U \cdot T/L \tag{1}$$

$$W = \tfrac{1}{2} \cdot L \cdot I^2 = \tfrac{1}{2} \times U^2 \cdot T^2/L \tag{2}$$

$$U_c = I \cdot \sqrt{L/C} \tag{3}$$

$$U_c = U/R_L \sqrt{L/C} \tag{4}$$

$$U_c/U = 2 \cdot \pi \cdot f \cdot L/R_L \tag{5}$$

$$2\pi f_o = \omega_o = 1/\sqrt{L \cdot C_o} \tag{6}$$

$$U_c/U = 1/\omega_o \cdot R_L \cdot C_o \tag{7}$$

Denoted therein are:
I(t)—the current value dependent on time,

L—the value of the inductance 14, $U_L(t)$—the elevated voltage apparing in time-dependent fashion at the switch 5, T—the time duration or closing time of the switch, W—the energy stored in the inductance 14, C—the electrical capacitance value of the sound generator 1, $U_C$—the electrical voltage across the sound generator 1 given a closed switch 5, $R_L$—ohmic resistance of the inductance 14, $f_o$—the resonant frequency to be excited.

The element 6 can be a timing element with which the closing time T is in turn defined. A further development of the invention is to control the closing time T automatically by means of evaluating the charging current curve of the inductance 14. This is shown in FIG. 3. The switch 5 is actuated by a storage flip-flop circuit 26. The flip-flop is set by an external "one" pulse. The switch 5 is closed as a result thereof and a current I(t) which rises linearly with time t (until the time T has elapsed) flows through the inductance 14. The current I through the inductance 14 is monitored by means of a current sensor 27. The flip-flop 26 is reset by the threshold switch 28 when a prescribed limit current is exceeded. The switch 5 opens and thus interrupts the current I(t) at t=T.

A number of considerable advantages are achieved with the invention. First, the excitation circuit according to FIG. 2 as well as according to FIG. 3 can be realized with little expense. The excitation energy W is independent within broad limits of the operating voltage applied to the terminals 2 and 3. The on-time T can result automatically and requires no special technique. The excitation of the sound generator 1 occurs with high excitation voltage without a particular resulting expense.

Further important advantages of the invention are that no unwanted modes appear in the oscillation excitation of the sound generator 1. High-frequency unwanted modes are not excited because the voltage change at the sound generator 1 does not occur suddenly in the invention. Low-frequency unwanted modes are not excited because the electrical voltage surge within an oscillation period of a low-frequency oscillation mode is compensated by a respectively further voltage surge having the opposite polarity. Special balancing is not required for the invention.

Advantages even result from the invention when sound generator 1 is employed as a sound receiver. The self-capacitance C of the sound generator 1 and the inductance L provided according to the invention form a selection circuit for the desired useful mode of the mechanical receive oscillation to be generated in the sound generator given reception.

An excitation circuit according to the invention can, for example, be operated with 12 volts d.c. at the terminals 2 and 3. FIG. 4 shows a practical circuit diagram. Circuit information permitting an average person skilled in the art to perform the invention is contained in FIG. 4.

Figure 5:
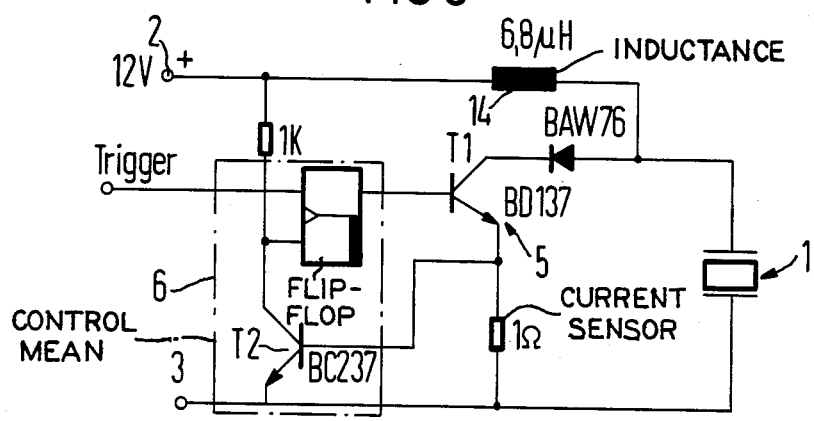

FIG. 5 shows the practical circuit of a further embodiment of the invention. FIG. 5 likewise contains the data specifications required for the average person skilled in the art. The coupling to the coil occurs via a switch diode, for example BAW 76, in order to avoid a short of the applied voltage at the transistor $T_1$ which is then operated inversely given overshooting of the electrical voltage at the sound generator. This diode decouples the sound generator from the transistor $T_1$ given negative voltages. A voltage of 150 volts is generated at the sound generator 1 with the illustrated excitation circuit.

Figure 6:
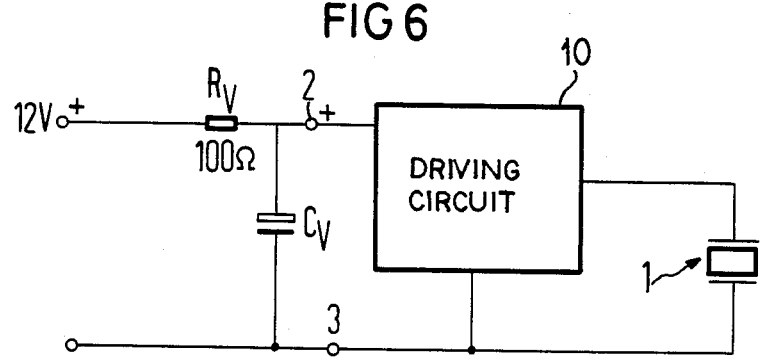
FIG. 6 is a circuit diagram of another embodiment of the invention.

FIG. 6 shows a series circuit for the supply voltage between the terminals 2 and 3. The series circuit comprises a resistor $R_V$ and a capacitor $C_V$. This series circuit prevents the supply voltage between the terminals 2 and 3 from being shorted by the inductance 14 in the driving circuit 10 (similar to FIG. 5) given an operationally occurring short at the sound generator 1. A value of $2(W/U^2)$ is recommended for the capacitor $C_V$.

Although various minor changes and modifications might be proposed by those skilled in the art, it will be understood that I wish to include within the claims of the patent warranted hereon all such changes and modifications as reasonably come within my contribution to the art.

I claim as my invention:

1. An excitation circuit, comprising:
a piezo-electric sound generator;
power supply terminals;
an inductance in series with the sound generator between the power supply terminals;
switch means in parallel with said sound generator, and in series with said inductance across said power supply terminals;
a value of said inductance and a value of a capacitance of said sound generator being chosen with respect to one another such that a tuned frequency of a resulting oscillation circuit formed by said inductance and sound generator capacitance is identical to a predetermined resonant frequency of said sound generator.

2. An excitation circuit according to claim 1 wherein control means for electronic actuation control of said switch means is connected to said switch means.

3. An excitation circuit according to claim 2 wherein said control means comprises a flip-flop circuit.

4. An excitation circuit according to claim 3 wherein said flip-flop circuit is controlled by connection to a threshold switch means for responding to a current flowing through said inductance when said switch means is closed.

5. An excitation circuit, comprising:
a piezo-electric sound generator;
a power supply having first and second terminals;
an inductor connected in series with the sound generator across the first and second terminals;
switch means connected in parallel with the sound generator and in series with the inductor for periodically connecting the inductor across the supply voltage terminals; and
an inductance of the inductor being chosen such that in combination with a capacitance of the sound generator a tuned circuit is formed having a frequency identical to a resonant frequency of the sound generator.

6. An excitation circuit according to claim 5 wherein said switch means comprises a flip-flop having a first input connected to a trigger and a second input connected to a threshold means, and an output connected to control a semiconductor switch; and said threshold means including a current sensing means in series with the semiconductor switch for determining when a predetermined current level is flowing through the inductor.

* * * * *